United States Patent
Lampersberger et al.

(12)

(10) Patent No.: US 6,535,279 B1
(45) Date of Patent: Mar. 18, 2003

(54) MEASURING DEVICE FOR THE QUALITY CONTROL OF PRINTED PRODUCTS

(75) Inventors: Franz Lampersberger, Aschheim (DE); Karsten Wendt, Obertshausen (DE); Bernd Tielebörger, München (DE); Rainer Tutsch, München (DE); Peter Rakitsch, Moosburg (DE); Hans Joachim Six, München (DE); Jörg Sierks, München (DE)

(73) Assignee: MAN Roland Druckmaschinen AG (DE)

( * ) Notice: Subject to any disclaimer, the term of this patent is extended or adjusted under 35 U.S.C. 154(b) by 323 days.

(21) Appl. No.: 09/662,088

(22) Filed: Sep. 14, 2000

(30) Foreign Application Priority Data

Oct. 22, 1999 (DE) ....................... 299 18 640 U

(51) Int. Cl.$^7$ ............................ G01J 3/50; G01N 21/47
(52) U.S. Cl. ..................... 356/73; 356/402; 356/446
(58) Field of Search .................. 356/73, 446, 402, 356/405, 406, 407, 425, 319, 326, 328; 250/226

(56) References Cited

U.S. PATENT DOCUMENTS 6,018,385 A * 1/2000 Lampersberger et al. ..... 356/73

* cited by examiner

*Primary Examiner*—F. L. Evans
(74) *Attorney, Agent, or Firm*—Leyidg, Voit & Mayer, Ltd.

(57) ABSTRACT

A measurement device is described for the quality control of printed products, having a pair of optical channels that differ in their properties and operate simultaneously. Each optical channel comprises an illumination channel for illuminating a measurement location and a reflection channel that picks up the light reflected from the measurement location. The reflected light is directed to an evaluation unit, which is connected to the reflection channel, that analyzes the reflected radiation spectrally. Polarization filters arranged in one of the pairs of channels provides the difference in the optical properties between the two pairs of channels. The measuring device provides an increased number of obtainable measured values for further processing in a way that requires only a modest increase in the metrological outlay compared to other measuring devices of this type.

19 Claims, 1 Drawing Sheet

MEASURING DEVICE FOR THE QUALITY CONTROL OF PRINTED PRODUCTS

TECHNICAL FIELD OF THE INVENTION

The present invention relates to a measuring device for the quality control of printed products.

BACKGROUND OF THE INVENTION

For a long time, densitometry has been used for controlling the quality of printed products and, in particular, of offset printed products. According to typical densitometry measurement techniques, a measurement field is illuminated at an angle of 45° degrees to the surface of the field and reflected light is detected by spectrophotometer at an angle of 0° degrees. This is commonly known as 45/0 geometry. The converse geometry is known as 0/45 geometry.

In one technique, radiation derived from the measurement field includes the color of the field is obtained and used to determine the absorption of radiation in the measurement field. The spectrophotometer signal can be converted into densitometry values by a photoelectric converter and a downstream evaluation unit.

This technique of measuring color density, which is widely used in offset printing, is practical for glossy printing since there is a relationship between the measured optical density and the thickness of the ink on the printed sheet. Therefore, these densitometry values are amenable for controlling the feeding of ink.

Because of the angles of incidence, the reflected light may include the gloss of the wet ink. This "glossy effect" of the wet ink often affects the accuracy of the measurement unless there is some compensation for the effect. In order to suppress the glossy effect in freshly printed inks, the polarization planes of polarization filters are in a crossed arrangement in the illumination and reflection channels. By suppressing the glossy effect in the light reflected from freshly printed inks, the measured values from fresh and dried inks can be equated.

In addition to measuring the densitometry values on a printed product, measuring calorimetric values have been increasingly used for controlling the quality of printed products. Colorimetric values are measured by either a tristimulus based colorimeter or by a spectrophotometer combined with digital weighting. Colorimetric values are used to control inks of both scaled colors and special colors, and also are used to attain expected color loci.

Colorimeters based on the tristimulus method are compact and simple in structure, but are suitable only for colored samples. In a spectrophotometer, however, reflected light from the measurement field is split up and digitally weighted according to a pre-selected function, thereby providing for any desired filter curve. Thus, for a spectrophotometer, both colorimeter and densitometry values can be obtained, depending on the filter curves applied.

The standards on which the color measurement is based do not provide for the use of polarization filters, because of the intended simulation of the human visual sense. Consequently, spectrophotometers that function as colorimeters and densitometries are either not equipped with polarization filters, or are equipped with switchable polarization filters in a complicated way, which increases the constructional outlay or measurement time considerably.

German patent no. DE 88 16 978 U1 discloses a measuring instrument, which can be moved in the X- and Y-direction, such that any desired locations on printed sheets can be measured. The measuring instrument has two measuring heads. One of the heads is for measuring density and the other is for measuring color. A three-color simultaneous measuring head measures the ink density and a tristimulus-based measuring head measures the color. Neither the three-channel densitometry measuring head or the tristimulus-based measuring head provide a purely spectral measured value. Thus, the use of this equipment is restricted.

In German patent no. DE 195 30 185 A1, a device for measuring the color of prints in offset printing includes an illumination channel with a polarization filter for illuminating the measurement location perpendicularly. Receiving channels, with or without a polarization filter, receive the light reflected from the measurement point at an angle of 45° degrees. Although this device is compact in design and construction, it has the disadvantage of requiring the illuminating light to be polarized. For colorimetric values to be derived form the reflected light, however, it is generally not possible to use measured values obtained with polarized light in the irradiation. Thus, this measuring device is also limited in its applications.

SUMMARY OF THE INVENTION

According to the invention, a measurement device is provided whose applications to quality control techniques for off-set printing is significantly enhanced with respect to the devices previously known. The measuring device includes two illumination channels that operate simultaneously, but have different optical properties. One of the channels includes one or more polarization filters to remove the "glossy effect" of wet ink and the other does not. The illumination channel with polarization filters is associated with a receiving or reflection channel that likewise includes polarization filters. These filters are conventional linear polarization filters. The illumination channel without the polarization filters is associated with a receiving or reflection channel that is also without polarization filters.

A location on the measurement field of a print is measured for ink thickness using the reflection spectra of the reflection channels having the polarization filters and measured for calorimetric values using the illumination and receiving channels without polarization filters. These channels operate simultaneously and eliminate the need for switching polarization filters and the associated successive measurements necessitated by this switching.

Several advantages immediately derive from the simultaneous use of two separate channels. First, both spectra and colorimetric values can be obtained for the measurement fields for the non-polarized channel. Second, by measuring at the measurement location with both polarized and non-polarized channels, spectral measured values are obtained that can be used to assess and compensate for the drying properties of individual inks and overprints. Third, any desired filters can be generated in the non-polarized receiving channels. Therefore, not only scale colors but also special colors can be controlled and/or measured in the respective highest absorption range.

The illumination channels are fed from a central lamp unit. The channels comprise optical waveguides and optics that illuminate the measurement locations. In one channel, a polarization filter is arranged in the beam path of the respective illumination optics. The illumination of the measurement locations in both illumination channels is preferably carried out at an angle of 45° by conventional annular optics.

Radiation reflected from the measurement location is fed via the optical waveguides to evaluation units, which are provided with opto-electrical converters. Since the illumination of the measurement field takes place at a 45° angle, the reflected radiation is perpendicular to the field. Thus the reflected channels are positioned accordingly in order to capture the reflected radiation. Arranged upstream of the optical waveguides are suitable optics for picking up (e.g., focusing) the radiation reflected from the measurement field.

The reflection channel that includes a polarization filter passes the reflected radiation to an evaluation unit such as a spectrophotometer. Because the reflected light has been compensated for the "glossy effect," the evaluation unit can accurately determine ink density using convention evaluation techniques. Also, in the evaluation unit, the filtered radiation from the central lamp unit can be analyzed in order to compensate, in a well-known manner, for the influences of the lamp spectrum.

The radiation received through the reflection channel without a linear polarization filter is likewise fed via an optical waveguide to a spectrophotometer or a standard colorimetric evaluation unit. The colorimetric evaluation unit analyzes the radiation spectrally using conventional techniques (e.g., numerical weighting of the individual spectral regions).

Thus, the measuring head of the invention provides for the simultaneous collection of data from which both color and ink-density analyses are performed.

Additional features and advantages of the invention will be made apparent from the following detailed description of the illustrative embodiment that proceeds with reference to the accompanying FIGURE.

BRIEF DESCRIPTION OF THE DRAWINGS

While the appended claims set forth the features of the present invention with particularity, the invention, together with its objects and advantages, may be best understood from the following detailed description taken in conjunction with the accompanying drawing which illustrates, in basic form, the components of the measuring device according to the invention.

DETAILED DESCRIPTION OF THE INVENTION

Figure 1:
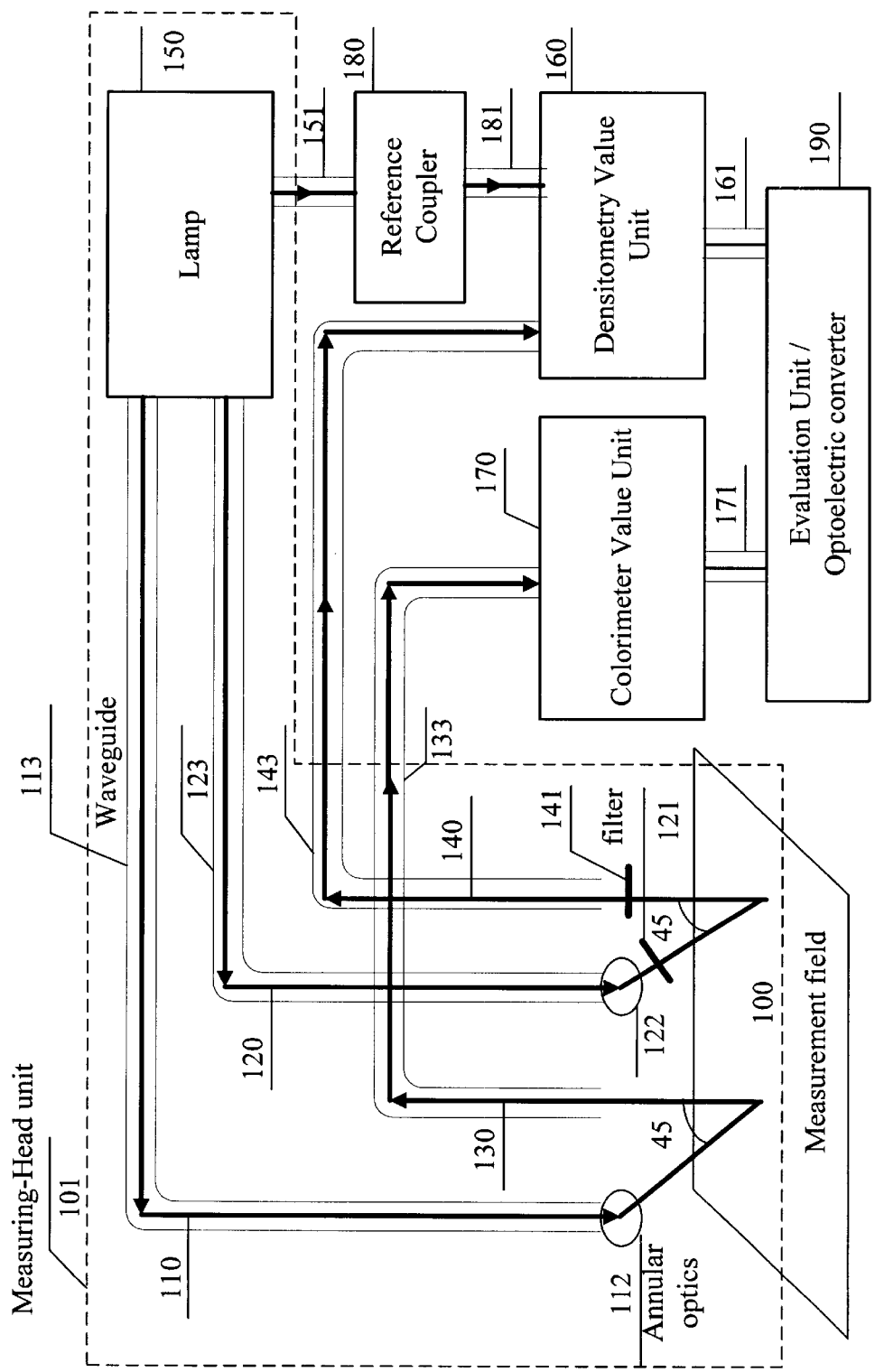

Turning to the drawings and referring to the single drawing FIGURE, FIG. 1, arranged in a measuring-head unit 101 are two illumination channels 110 and 120, which irradiate a measurement field at a 45° angle as indicated in the FIGURE. The illumination channels 110 and 120 preferably comprise annular optics 112 and 122, respectively. The radiation illuminating the measurement locations on the measurement field are provided by a central lamp unit 150 via optical waveguides 113 and 123.

Arranged in the illumination channel 120 is a linear polarization filter 121, which polarizes the light from the lamp 150 before it strikes the measurement field 100.

The illumination channels 110 and 120 are assigned reflection channels 130, 140 through which the light reflects perpendicularly from the respective measurement locations of the measurement field 100. the reflection channels 130 and 140 lead to a spectral evaluation unit 160 and a colorimetric evaluation unit 170. The radiation from the measurement locations of the measurement field 100 is forwarded via conventional and well-known optical waveguides 133 and 143. Connected upstream of the optical waveguides 133 and 143 are optical components (not shown) that couple the reflected radiation from the measurement location into the waveguides. Optical components of this type are known and therefore do not require any further explanation.

Arranged in the beam path of the reflection channel 140 is a linear polarization filter 141. Only the polarized component of the radiation reflected from the measurement location is led via the optical waveguide to the spectral evaluation unit 160.

The central lamp unit 150 is connected via optical waveguides to the illumination channels 110 and 120. Via a further optical waveguide 151 and a reference coupler 180, the radiation from the central lamp unit 150 is also delivered to the spectral evaluation unit 160, which may be a spectrophotometer. The radiation fed directly to the spectral evaluation unit 160 from the lamp 150 provides the unit with the spectrum of the light from the lamp 150, which can be compared with the spectrum of the light received via the reflection channel 143.

The radiation from the reflection channel 130 (unpolarized) is fed via an optical waveguide to the colorimetric evaluation unit 170, where the radiation is analyzed either by means of physical filters or calorimetrically by a spectrophotometer using digital weighting. The output signals from the spectral evaluation unit 160 and from the calorimetric evaluation unit 170 are fed to an evaluation unit 190, which accumulates and stores the measured signals, converts the signals into appropriate variables by means of predefined formulae or feeds the signals to a display (not illustrated).

According to the invention, densitometry measurement and colorimeter measurement are conducted simultaneously, with filters and without filters respectively. The calorimeter measurement unit 170 is either a spectrophotometer or a standard colorimeter evaluation unit. The calorimeter evaluation unit 170 can analyze the spectral radiation with numerical weighting of the individual spectral region.

Linear polarization filters 121 and 141 are assigned to illumination channel 120 and reflection channel 140. The two polarization filters are mounted in the channels so that their polarization planes are crossed or orthogonal to one another. By feeding the reflection channel 130 without filter into the calorimeter value unit 170 and the reflection channel with polarization filter 140 into the densitometry value unit conjointly, densitometry values and colorimeter values from the measurement field 100 are obtained at the same time. Densitometry values are used to access and compensate the properties of individual inks and overprints.

According to this invention, the filters 121 and 141 are not limited to linear polarization filters but can be any desired filter. Therefore, both scaled colors and special colors can be controlled or measured within a relatively high absorption range.

Typically, the measurement field 100 is illuminated at an angle of 45° degrees to the surface and reflection light is measured at an angle of 0° degree, which is known as 45/0 geometry (the converse is 0/45 geometry). The illustrated embodiment of this invention provides 45/0 geometry. But the invention may alternatively employ the 45/0 geometry. Illumination channels 110 and 120 are focused onto the measurement field 100 by annular optics 112 and 122, which are of conventional design. Reflection channels 130 and 140 coupled by the upstream waveguides as 133 and 143 respectively, are detected perpendicularly to the measurement field.

All of the references cited herein, including patents, patent applications, and publications, are hereby incorporated in their entireties by reference.

In view of the possible alternative embodiments to which the principles of this invention may be applied, it should be recognized that the embodiment described herein with respect to the drawing FIGURE is mean to be illustrative only and should not be taken as limiting the scope of invention. Therefore, the invention as described herein contemplates all such alternative embodiments as may come within the scope of the following claims and equivalents thereof.

We claim:

1. A device for measuring attributes of printed products comprising (1) a first pair of illumination and reflection channels for illuminating a measurement location on a printed product and gathering radiation reflected from the location (2) a second pair of illumination and reflection channels for illuminating the same or different measurement location on the printed product and gathering radiation reflected from the location, (3) at least one evaluation unit for analyzing the reflected radiation from both pairs of channels, and (4) at least one polarization filter arranged in only one of the pairs of illumination and reflection channels.

2. The measuring device according to claim 1 wherein the one pair of illumination and reflection channels includes a polarization filter in each of the illumination and reflection channels.

3. The measuring device according to claim 1 wherein both of the illumination channels are illuminated by a single source.

4. The measuring device according to claim 1 wherein each of the illumination channels includes optical waveguides.

5. The measuring device according to claim 1 wherein each of the reflection channels includes optical waveguides.

6. The measuring device according to claim 1 including means for providing to a calorimetric evaluation unit the radiation from the pair of illumination and reflection channels that does not include a polarization filter.

7. The measuring device according to claim 1 including means for feeding to a spectrophotometric evaluation unit the radiation from the pair of illumination and reflection channels that includes the polarization filter.

8. The measuring device according to claim 1 including a reference coupler for feeding radiation from a source of radiation for illuminating the pairs of illumination and reflection channels directly to the evaluation unit.

9. The measuring device according to claim 1 wherein each of the pairs of the illumination and reflection channels provides radiation to a respective evaluation unit, where the evaluation unit for the pair of illumination and reflection channels that include a polarization filter provides radiation to a unit that measures densitometry values and the pair of illumination and reflection channels that does not have a polarization filter provides radiation to a unit that measures colormetric values.

10. The measuring device of claim 9 wherein the two evaluation units provide measured densitometry and calorimetric values of the printed product from radiation received from the pairs of illumination and reflection channels to a third evaluation unit that processes the measured values jointly.

11. A method for measuring the quality of a printed product comprises the steps of:

simultaneously illuminating a measurement location on the product by both un-polarized and polarized illumination light;

measuring densitometry values from polarized reflection light from the measurement location and calorimeter values from the un-polarized reflection light from the measurement location; and applying the densitometry values and calorimeter values to an evaluation unit.

12. A measurement device for evaluating printing quality in a printed product comprising unpolarized and polarized illumination channels illuminating a measurement location of a printed product; un-polarized and polarized reflection channels receiving reflected light from the measurement location; and evaluation units connected to the reflection channels for analyzing the reflected light signals spectrally to provide both densitometry and colorimetric measurements of the printed product.

13. The measurement device of claim 12 wherein polarized illumination light is obtained by arranging a linear polarization filter in the polarizing illumination and reflection channels.

14. A measurement device of claim 12 wherein the un-polarized and polarized illumination channels receive radiation from a radiation generator.

15. A measurement device of claim 12 wherein the un-polarized and polarized illumination and reflection channels include optical waveguides to conduct the radiation.

16. The measurement device of claim 12 wherein one of the evaluation units includes a spectrophotometer.

17. The measurement device of claim 16 wherein the spectrophotometer is connected to the polarized reflection channel.

18. The measurement device of claim 12 wherein a colorimeter evaluation unit is connected to the un-polarized reflection channel.

19. The measurement device of claim 16 further including a coupler for coupling to the spectrophotometer radiation from a source of radiation for the polarized and un-polarized illumination channel.

* * * * *